United States Patent [19]

Jenkins et al.

[11] 4,207,254
[45] Jun. 10, 1980

[54] METHOD FOR PREPARING IMPROVED TOLUENE SULFONIC ACID DERIVATIVES AND THE PRODUCTS THEREOF

[75] Inventors: Harry L. Jenkins, Huntington, W. Va.; Gene C. Smelser, Proctorville, Ohio; David W. Alford, Milton, W. Va.

[73] Assignee: BASF Wyandotte Corporation, Wyandotte, Mich.

[21] Appl. No.: 670,939

[22] Filed: Mar. 26, 1976

[51] Int. Cl.$^2$ .......................................... C07C 143/56
[52] U.S. Cl. ................................................. 260/508
[58] Field of Search ........................................ 260/508

[56] References Cited

U.S. PATENT DOCUMENTS

| 1,755,648 | 4/1930 | Henle et al. | 260/508 |
| 1,773,706 | 8/1930 | Henle et al. | 260/508 |
| 1,917,441 | 7/1933 | Fischer et al. | 260/508 |
| 1,947,837 | 2/1934 | Fischer et al. | 260/508 |
| 3,123,645 | 3/1964 | Hogenboecker | 260/508 |
| 4,014,866 | 3/1977 | Henning | 260/508 |

FOREIGN PATENT DOCUMENTS 2240849   3/1974   Fed. Rep. of Germany ........... 260/508

OTHER PUBLICATIONS

Lepri et al., J. Chromatography, vol. 88 pp. 331–339, (1974).

*Primary Examiner*—Norman Morgenstern
*Assistant Examiner*—James H. Reamer
*Attorney, Agent, or Firm*—Joseph D. Michaels

[57] ABSTRACT

Improved toluene sulfonic acid derivatives are precipitated at a constant pH from an aqueous salt solution.

11 Claims, No Drawings

METHOD FOR PREPARING IMPROVED TOLUENE SULFONIC ACID DERIVATIVES AND THE PRODUCTS THEREOF

BACKGROUND OF THE INVENTION

This invention relates to toluene sulfonic acid derivatives having improved physical properties. More particularly this invention relates to 2-chloro-5-amino-para-toluene sulfonic acid, 4-amino-meta-toluene sulfonic acid, and 6-chloro-4-amino-meta-toluene sulfonic acid having improved physical properties. This invention also relates to an improved method for obtaining said toluene sulfonic acid derivatives from aqueous solutions of their respective salts.

In one commercial process for making said toluene sulfonic acid derivatives, the desired compound is precipitated in a batch-wise manner from an aqueous salt solution of such compound by adding slightly more than the stoichiometric amount of a mineral acid in one charge to the total batch of salt solution and allowing the pH of the mixture to decrease as the reaction proceeds. The precipitate is usually removed by filtration in the form of a wet presscake which, due to its low bulk density and the affinity of the product for water, requires long lengths of time to be dried.

The dried product which results from the foregoing process has many undesirable physical properties. Such a product is, for example, extremely difficult to handle due to its dusting characteristics and is also difficult to use in further synthesis procedures due to its resistance to wetting. Such a resistance to wetting makes the formation of solutions containing such a product very difficult, even with the use of wetting agent. It is also impractical to use the wet presscake which is formed by the foregoing procedure directly in the synthesis of pigmentary compositions due in part to the large amounts of water retained therein and the non-uniformity of the presscake which makes a reliable assay impossible.

SUMMARY OF THE INVENTION

It is, therefore, an object of this invention to provide toluene sulfonic acid derivatives having improved physical characteristics.

Another object of this invention is to provide low-dusting toluene sulfonic acid derivatives.

A further object of this invention is to provide a wet presscake of a toluene sulfonic acid derivative which may be used directly in the synthesis of pigmentary compositions.

A still further object of this invention is to provide an improved method for obtaining said toluene sulfonic acid derivatives from aqueous solutions of their respective salts.

The foregoing and the other objects may be accomplished by a process for precipitating a toluene sulfonic acid derivative selected from the group consisting of 2-chloro-5-amino-para-toluene sulfonic acid, 4-amino-meta-toluene-sulfonic acid, and 6-chloro-4-amino-meta-toluene sulfonic acid from an alkali metal salt solution of said derivative, said process comprising precipitating said derivative at an essentially constant pH of from about 0.5 to about 1.2. Preferably the precipitation is performed at a pH of from about 0.8 to about 1.2. A range of from about 0.9 to about 1.1 is especially preferred.

DESCRIPTION OF A PREFERRED PROCESS

In a typical process for preparing an aqueous solution of an alkali metal salt of 2-chloro-5-amino-4-toluene sulfonic acid, toluene is first reacted with sulfuric acid to produce para-toluene sulfonic acid as the principal product. The sulfonic acid is then reacted with chlorine to produce 2-chloro-para-toluene sulfonic acid as a principal product which is reacted with a mixture of 50 percent nitric acid and 50 percent sulfuric acid to produce 2-chloro-5-nitro-para-toluene sulfonic acid. The nitrated product is then neutralized in an aqueous lime slurry which is subsequently filtered. The aqueous nitrated product is then iron reduced to form an amine and the reaction mixture is neutralized with sodium hydroxide to a pH of about 9.5–10.5 and the resulting solution is subsequently filtered.

In a typical process for preparing an aqueous solution of an alkali metal salt of 4-amino-meta-toluene sulfonic acid, para-toluidine is mixed with trichlorobenzene and then sulfonated with sulfuric acid to form a mixture of the desired product in trichlorobenzene. The product mixture is subsequently mixed with an aqueous solution of sodium hydroxide and the trichlorobenzene phase is removed, thus leaving an aqueous salt solution of 4-amino-meta-toluene sulfonic acid.

In a typical process for preparing an aqueous solution of an alkali metal salt of 6-chloro-4-amino-meta-toluene sulfonic acid, 2-chloro-4-amino toluene is mixed with trichlorobenzene and sulfonated with sulfuric acid to form a mixture of the desired product in trichlorobenzene. The product mixture is subsequently mixed with an aqueous solution of sodium hydroxide and the trichlorobenzene phase is removed, thus leaving an aqueous salt solution of 6-chloro-4-amino-meta-toluene sulfonic acid.

From the foregoing general description, it is apparent that the specified toluene sulfonic acid derivatives all exist in an aqueous salt solution from which the desired product may be precipitated. Conventionally the product is precipitated from such an aqueous salt solution by simply adding a mineral acid, such as hydrochloric acid, batch-wise to said solution to obtain a final pH of from about 0.5 to about 1.2. During such a precipitation the pH of the salt solution varies widely from an initial pH of about 8.5–9.5 to the final pH of about 0.5–1.2. The product is then usually filtered to form a presscake which is washed with water and dried. The presscake formed by the foregoing method has a low bulk density and is non-uniform with respect to the amount of product contained per unit volume. The presscake is also "muddy", difficult to wash, and impractical to use directly in further synthesis procedures. The final dried product obtained by such procedure is extremely dusty and essentially non-wettable.

For the purposes of this invention, the term alkali metal salt means a sodium or potassium salt of the contemplated toluene sulfonic acid derivative. Further, when the term mineral acid is used herein it means hydrochloric acid, sulfuric acid and nitric acid.

It has now been discovered that it is possible to produce toluene sulfonic acid derivatives, and presscakes thereof, which do not have the foregoing disadvantages by utilizing a process by which the precipitation of the desired product from an aqueous alkali metal salt solution is done at a substantially constant pH from about 0.5 to about 1.2.

In a preferred embodiment of the process of this invention, the aqueous alkali metal salt solution containing the desired product and the mineral acid, e.g., hydrochloric acid, are incrementally mixed at a rate such that the pH of the mixture is maintained from about 0.5 to about 1.2. The term "incrementally mixed" is used herein to refer to a process whereby the aqueous alkali metal salt solution and the mineral acid are mixed by physically combining distinct aliquots or continuous streams thereof. Most preferably, continuous streams of the salt solution and the mineral acid are mixed at a rate such that the pH of the mixture is maintained from about 0.5 to about 1.2.

The optimum pH range will vary depending upon the particular toluene sulfonic acid derivative that is being precipitated. For 2-chloro-5-amino-para-toluene sulfonic acid, a pH of from about 0.5 to about 1.2 is preferred, and most preferred is a pH from about 0.9 to about 1.1. For lower molecular weight toluene sulfonic acids, it is anticipated that a lower pH range may be operable and for higher molecular weight toluene sulfonic acids, it is anticipated that a higher pH range may be operable. It will be readily apparent that a pH which is outside of the above-mentioned range may be operable depending upon the rate of mixing, the temperature, the substrate, the acid and other variable conditions. The rate of addition and temperature during mixing are not contemplated as being critical. Usually the precipitation is performed at a temperature of from about 50° C. to about 80° C.

A more detailed understanding of the invention may be obtained by referring to the following Example I which describes a constant pH precipitation of 2-chloro-5-amino-para-toluene sulfonic acid from an aqueous salt solution thereof.

EXAMPLE I

Four liters of a sodium salt solution of 2-chloro-5-amino-para-toluene sulfonic acid which was produced in the manner described above and having a pH of about 9.3 is heated to about 70° C. and placed in a dropping funnel. The salt solution is added dropwise to a beaker (equipped with a mechanical stirrer) while concurrently adding 150 milliliters of hydrochloric acid (20° Be) dropwise at a rate sufficient to maintain the pH of the mixture in the beaker within the range of about 1.0–1.5. After the addition is complete, the mixture is stirred for an additional hour at a temperature of about 70° C. The mixture is then filtered and the resulting presscake washed first with 1750 milliliters of water, then a solution of 50 milliliters of one percent Aerosol OT (trademark of American Cyanamid) surfactant in 200 milliliters of water. The washed presscake is then dried at 90° C. and screened. 98.6 grams of 2-chloro-5-amino-para-toluene sulfonic acid is obtained.

For purposes of comparison, a batch precipitated product is produced from four liters of the same batch of plant produced sodium salt solution of 2-chloro-5-amino-para-toluene sulfonic acid, as was utilized in Example I. A method identical to that of Example I is followed to obtain the desired product except the hydrochloric acid is added in batch, to the total quantity of salt solution. 99.8 grams of 2-chloro-5-amino-para-toluene sulfonic acid is obtained.

It was noted that although the weight of the product obtained in Example I was almost the same as the weight of the batch precipitated product, the volume occupied by the product of Example I was approximately one-half of the volume occupied by the batch precipitated product. Thus, the product of Example I had a dry bulk density that was approximately twice that of the batch precipitated product. It was also noted that the product of Example I when compared to the batch precipitated product, settled faster after precipitation, washed faster, and screened faster and easier. Upon microscopic comparison of the two products it was determined that the agglomerates of the product of Example I were uniform in size and had an ellipsoidal shape whereas the agglomerates of the bulk precipitated product were very irregular in both shape and size. Presscake prepared in the plant in accordance with the process of Example I typically contains from about 60 percent to about 79 percent solids whereas plant presscake prepared by the batch precipitation process typically contains from about 42 percent to about 52 percent solids. The higher solids content of the presscake of the constant pH precipitated product and the correspondingly lesser amount of water makes it economically feasible to ship the presscake. Due to the lesser amount of water in the presscake of the constant pH precipitation product the amount of time required to dry the presscake has been substantially reduced.

A product was prepared on a plant scale in accordance with the method of Example I for determining the feasibility of using the wet presscake directly in further synthesis.

Red Lake C and other azo red pigments which are made with 2-chloro-5-amino-para-toluene sulfonic acid were prepared from the aforementioned presscake, utilizing the standard procedure for preparing such pigments.

A constant pH precipitation product was prepared in accordance with the method of Example I except no surfactant solution was utilized and the presscake was washed with approximately one-half of the volume of water used to wash the presscake in Example I. The aforementioned constant pH precipitation product was compared to a product which was prepared in accordance with the foregoing batch precipitation method except the presscake was washed in the same manner as described for the constant pH precipitation product. The results are summarized in Table I.

TABLE I

| | Constant pH Precipitation Product | Batch Precipitation Product |
|---|---|---|
| Dry Bulk Density-Product (grams of screened dried product/cc of dry product) | 0.44±15% | 0.16±15% |
| Wet Bulk Density-Presscake (grams of dried product/cc of wet presscake) | 0.18±10% | 0.08±10% |
| Absolute Crystal Density (grams of crystalline product/cc of crystalline product) | 1.5±10% | 0.7±10% |

The dry bulk densities of the products were obtained by filling a container, having a known volume and tare weight, with dried product which had been passed through a 20 mesh screen, and weighing the combined weight of the container and product. The dry bulk density was then obtained by simple arithmetic computation. It was surprisingly found that the dry bulk density of the constant pH precipitation product was more than 2.5 times greater than the dry bulk density of the batch precipitation product.

The wet bulk densities of the presscakes of the products were obtained by depositing the presscakes on a Buchner funnel. The volume was then determined by measuring the height of the presscake and the diameter of the funnel. The measured quantity of presscake was then transferred to a drying dish having a known tare weight and heated to obtain a dry product. The drying dish and dried product were then weighed. The wet density of presscake, expressed as grams of dried product per cubic centimeter (cc) of presscake was then obtained by simple arithmetic computation. Again, it was surprisingly found that the wet bulk density of the presscake of the constant pH precipitation product was over two times greater than the wet bulk density of the presscake of the batch precipitation product.

The crystal densities of the products were obtained by filling a container, having a known tare weight, to a given volume with a mixture of wet presscake and water and obtaining the combined weight. The measured quantity of presscake and water was then transferred to a drying dish having a known tare weight and heated to obtain a dry product. The drying dish and dried product were then weighed. The crystal densities of the products, expressed in grams of crystalline product per cubic centimeter of crystalline product, which volume represents the absolute volume occupied by the crystals, were then obtained by the following formula:

$$\frac{\left(\begin{array}{c}\text{Weight of Drying Dish}\\\text{and Dried Product}\end{array}\right) - \left(\begin{array}{c}\text{Tare Weight of}\\\text{Drying Dish}\end{array}\right)}{\left[\left(\begin{array}{c}\text{Container}\\\text{Volume}\end{array}\right) - \left[\left(\begin{array}{c}\text{Weight of}\\\text{Container}\\\text{and Wet}\\\text{Presscake}\end{array}\right) - \left(\begin{array}{c}\text{Combined}\\\text{Weight of}\\\text{Container}\\\text{and Dry}\\\text{Product}\end{array}\right)\right]\left[\begin{array}{c}\text{Specific}\\\text{Gravity}\\\text{of}\\\text{Water}\end{array}\right]\right]}$$

The foregoing indirect method of obtaining the absolute crystal density of the products is possible since only a negligible amount of product is dissolved in the water which is evaporated from the presscake mixture. It was also surprisingly found that the crystal density of the constant pH precipitation product was over two times greater than the crystal density of the batch precipitation product.

The constant pH precipitation product was analyzed and determined to be composed of agglomerates having an average particle size of 25 microns and substantially all of the agglomerates were within the range of about 10 microns to about 40 microns. The foregoing was in sharp contrast to the batch precipitation product which was composed of agglomerates having an average particle size of 50 microns with substantially all of the products in the size range from about 5 microns to about 100 microns. The constant pH precipitation thus yields a product which is composed of agglomerates which have a maximum size difference of 30 microns, for substantially all of the particles, whereas the batch precipitated product is composed of agglomerates which have a maximum size difference of 95 microns, for substantially all of the particles. It was also observed that the constant pH precipitation product was less dusty than the batch precipitation product.

While the invention has been described with reference to certain specific embodiments, it will be recognized by those skilled in the art that many variations are possible without departing from the spirit and scope of the invention.

What is claimed is:

1. A process for preparing a toluene sulfonic acid selected from the group consisting of 2-chloro-5-amino-para-toluene sulfonic acid, 4-amino-meta-toluene sulfonic acid, and 6-chloro-4-amino-meta-toluene sulfonic acid, comprising forming an aqueous solution of an alkali metal salt of said acid, providing a source of a mineral acid, and mixing incremental portions of said salt solution and said acid in proportions sufficient to maintain the mixture at an essentially constant pH of from about 0.5 to about 1.2.

2. The process of claim 1 wherein the alkali metal is sodium.

3. The process of claim 2 wherein the mineral acid is hydrochloric acid.

4. The process of claim 3 wherein the pH of the mixture is maintained at an essentially constant value of from about 0.9 to about 1.1

5. The process of claim 1 wherein continuous streams of the aqueous alkali metal salt solution and the mineral acid are mixed.

6. The process of claim 5 wherein the alkali metal is sodium, the mineral acid is hydrochloric acid and the pH of the mixture is maintained at an essentially constant value of from about 0.9 to about 1.1.

7. In a process for preparing a toluene sulfonic acid selected from the group consisting of 2-chloro-5-amino-para-toluene sulfonic acid, 4-amino-meta-toluene sulfonic acid and 6-chloro-4-amino-meta-toluene sulfonic acid, wherein the toluene sulfonic acid is precipitated from an aqueous solution of an alkali metal salt of said acid by the addition of a mineral acid to said solution, the improvement comprising precipitating said sulfonic acid at an essentially constant pH of from about 0.5 about 1.2.

8. The process of claim 7 wherein the aqueous solution is a sodium salt solution.

9. The process of claim 8 wherein the toluene sulfonic acid is precipitated with hydrochloric acid.

10. The process of claim 9 wherein continuous streams of the sodium salt solution and hydrochloric acid are mixed.

11. The process of claim 10 wherein the pH of the mixture is maintained at an essentially constant value of from about 0.9 to about 1.1.

* * * * *